United States Patent
Oakes et al.

(10) Patent No.: US 10,695,489 B2
(45) Date of Patent: Jun. 30, 2020

(54) FLUID DELIVERY SYSTEM

(71) Applicant: ViCentra B.V., Utrecht (NL)

(72) Inventors: Timothy William Oakes, Swansea (GB); Joseph Cefai, West Glamorgan (GB)

(73) Assignee: VICENTRA B.V., Utrecht (NL)

( * ) Notice: Subject to any disclaimer, the term of this patent is extended or adjusted under 35 U.S.C. 154(b) by 141 days.

(21) Appl. No.: 15/773,283

(22) PCT Filed: Dec. 12, 2016

(86) PCT No.: PCT/EP2016/080687
§ 371 (c)(1),
(2) Date: May 3, 2018

(87) PCT Pub. No.: WO2017/118538
PCT Pub. Date: Jul. 13, 2017

(65) Prior Publication Data
US 2018/0318506 A1    Nov. 8, 2018

(30) Foreign Application Priority Data

Jan. 6, 2016 (GB) .................................. 1600229.7

(51) Int. Cl.
*A61M 5/172* (2006.01)
*A61M 5/142* (2006.01)
*A61M 5/158* (2006.01)

(52) U.S. Cl.
CPC ........ *A61M 5/172* (2013.01); *A61M 5/14224* (2013.01); *A61M 5/14244* (2013.01);
(Continued)

(58) Field of Classification Search
CPC .... A61M 5/14248; A61M 2005/14268; A61M 2205/14
See application file for complete search history.

(56) References Cited

U.S. PATENT DOCUMENTS

| 4,395,259 A | 7/1983 | Prestele et al. |
| 8,641,672 B2 * | 2/2014 | Yodfat .............. A61M 5/14248 604/151 |

(Continued)

FOREIGN PATENT DOCUMENTS

| CN | 103796696 A | 5/2014 |
| WO | WO 02/40083 A2 | 5/2002 |

(Continued)

OTHER PUBLICATIONS

Jun. 27, 2016 UKIPO Search Report for GB 16 00229.7.
(Continued)

*Primary Examiner* — Laura A Bouchelle
(74) *Attorney, Agent, or Firm* — Hahn Loeser & Parks LLP

(57) ABSTRACT

There is provided a fluid delivery system (100), comprising a pump (102) for pumping fluid from a cartridge (400) to an outlet. The pump comprises a housing (302), a cartridge which can be removably attached to the housing, and a switch (308) for activating the pump. The switch is arranged such that attaching the cartridge to the housing activates the switch to automatically activate the pump. The system may also include a control unit for wireless connection with the pump.

13 Claims, 6 Drawing Sheets

(52) U.S. Cl.
CPC ........ *A61M 5/14248* (2013.01); *A61M 5/158* (2013.01); *A61M 2005/14268* (2013.01); *A61M 2005/1585* (2013.01); *A61M 2205/121* (2013.01); *A61M 2205/14* (2013.01); *A61M 2205/3561* (2013.01); *A61M 2205/3569* (2013.01); *A61M 2205/3584* (2013.01); *A61M 2205/50* (2013.01)

(56) References Cited

U.S. PATENT DOCUMENTS

| | | | |
|---|---|---|---|
| 9,561,324 B2* | 2/2017 | Estes | G16H 20/17 |
| 9,566,383 B2* | 2/2017 | Yodfat | A61M 5/14248 |
| 2008/0255516 A1 | 10/2008 | Yodfat et al. | |
| 2012/0249294 A1 | 10/2012 | O'Connor | |
| 2014/0114277 A1* | 4/2014 | Eggert | A61M 5/20 604/500 |
| 2015/0112264 A1 | 4/2015 | Kamen et al. | |
| 2015/0265765 A1 | 9/2015 | Yavorsky et al. | |

FOREIGN PATENT DOCUMENTS

| | | | | |
|---|---|---|---|---|
| WO | WO 03/047665 A1 | 6/2003 | | |
| WO | WO 09/016635 A2 | 2/2009 | | |
| WO | WO-2009016635 A2 * | 2/2009 | ........ | A61M 5/14248 |

OTHER PUBLICATIONS

Feb. 23, 2017 ISR for PCT/EP2016/080687.
Feb. 23, 2017 Written Opinion of Int'l Searching Authority PCT/EP2016/080687.
Mar. 13, 2020, Official Communication in connection with EP 16 809 402.7.
Apr. 26, 2020, Official Communication in connection with CN 2016 8007 8301.3.

* cited by examiner

FLUID DELIVERY SYSTEM

The present application is a § 371 submission of international application no. PCT/EP2016/080687, filed 12 Dec. 2016 and published in the English language on 13 Jul. 2017 with publication no. WO 2017/118538 A1, which claims the benefit of the filing date of GB 16 00229.7 filed 6 Jan. 2016.

TECHNICAL FIELD

The present invention relates to a fluid delivery system, for example an infusion system for the infusion of a liquid therapeutic product.

BACKGROUND

Infusion systems for the infusion of liquid therapeutic products into the human or animal body are known in the art, e.g. from U.S. Pat. No. 4,395,259. Such systems are particularly, though not exclusively, intended for the infusion of insulin into the body for diabetes therapy. The system has an infusion device which may be implanted or worn externally on the body, and a remote controller that can wirelessly monitor the function of the infusion device. The infusion device includes a pump, a reservoir of the therapeutic product, control electronics and a battery power supply.

Such devices tend to be relatively large in size and have a high electrical power requirement necessitating frequent replacement or recharging of the battery. Extended or frequent periods where a user cannot receive delivery of the therapeutic product due to refilling or replacement of the reservoir of therapeutic product, or replacement or recharging of the battery are undesirable from a medical standpoint and are inconvenient for the user.

SUMMARY OF INVENTION

The present invention is defined in the claims appended hereto.

According to a first aspect, there is provided a fluid delivery system comprising a pump, the pump comprising: a housing; a cartridge for storing fluid, the cartridge removably attachable to the housing; and a switch for activating the pump; wherein the switch is arranged such that attaching the cartridge to the housing activates the switch to automatically activate the pump.

By arranging the switch such that attaching the cartridge to the housing activates the switch, power can be conserved in the pump by ensuring that it is only activated when there is a supply of fluid to be pumped (i.e. from the cartridge).

In embodiments of the invention, detachment of the cartridge from the housing may cause the switch to be deactivated, either immediately or after a period of time. Thus power is again conserved by ensuring the pump is inactive in the absence of a supply of fluid.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
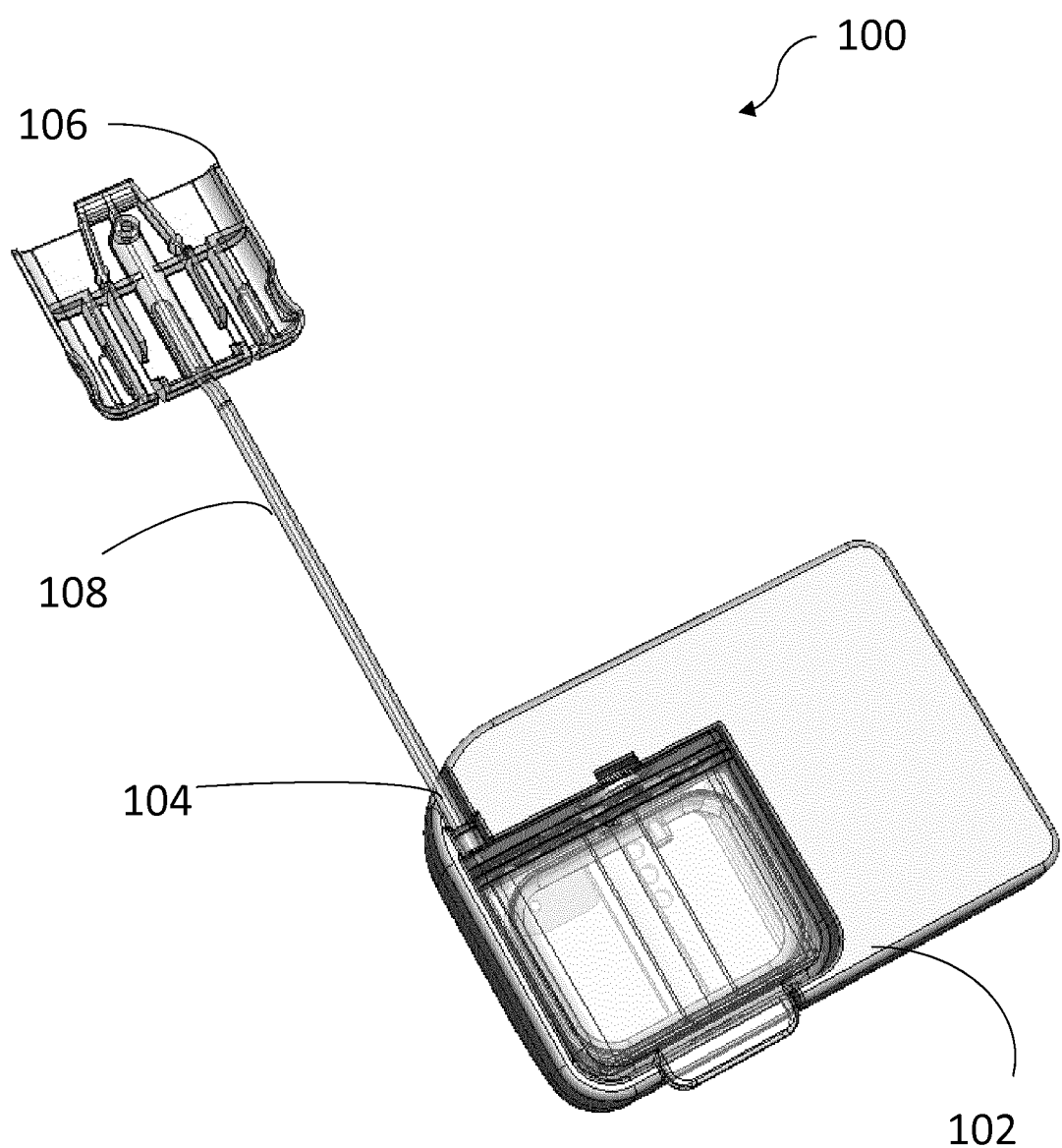
FIG. 1 shows a wearable part of an external infusion system, including an infusion set and a pump.

FIG. 1 shows the wearable part of an external infusion system 100 for the continuous subcutaneous infusion of insulin into the human body through repetitive small pulses of infusion. The infusion system 100 comprises a pump 102 having an outlet port 104 connected to an infusion set 106 via an infusion tube 108.

The infusion set 106 includes a subcutaneous cannula and an adhesive mount for adhering the infusion set to the patient's skin. The cannula is typically made of flexible plastic so as not to cause discomfort for the patient during use. The infusion set is typically installed into a spring loaded insertion device together with a steel needle surrounding the cannula. Upon insertion, the steel needle is removed leaving the cannula in place. Alternative infusion sets, which may replace the infusion set shown in FIG. 1, comprise a steel needle instead of the cannula.

Depending on the desired positioning of the pump 102 with respect to the infusion set 106 during use the length of the infusion tube 108 may be longer or shorter than that shown in FIG. 1, and indeed the infusion set 106 may be coupled directly to the output port 104 of the pump where close coupling of the infusion set 106 and the pump part 102 is desired, thereby avoiding the need for the flexible infusion tube 108.

Figure 2:
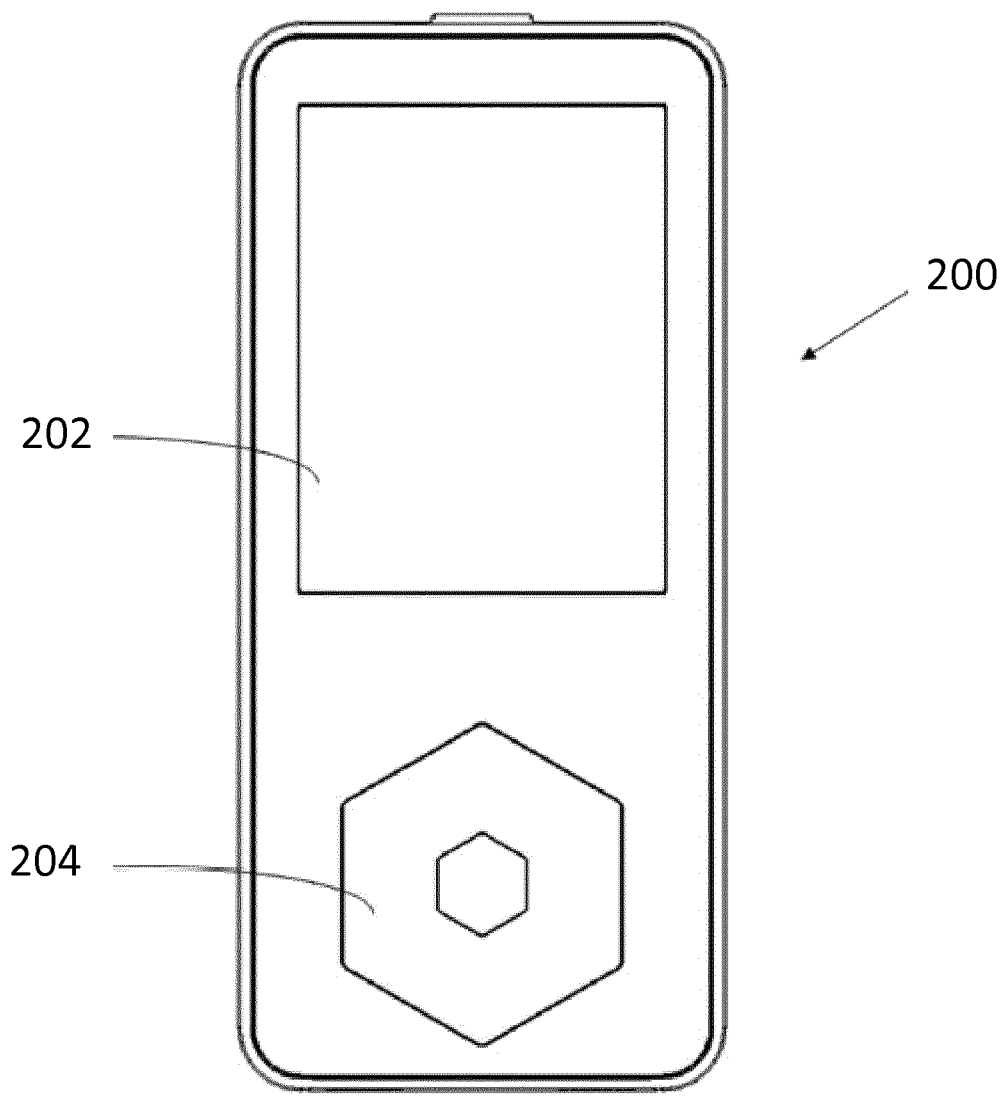
FIG. 2 shows a control unit of the infusion system for wireless communication with the wearable part.

The pump 102 may be wirelessly connected to a control unit 200 show in FIG. 2. The control unit 200 includes a transceiver for wireless communication with the pump 102. The wireless communication may be via Bluetooth™ or other radio frequency near field communication means. The control unit 200 includes a graphical user interface 202 and a tactile user interface 204. The control unit 200 enables a user to perform the following functions:

Define and store basal profiles;
Transfer an active basal profile to the pump 102;
Define and transmit a bolus request to the pump 102;
Define and transmit a temporary basal to the pump 102;
View a graphical recommendation of a bolus based on glucose readings from a separate blood glucose meter or entered manually following a blood glucose meter reading from a separate blood glucose meter (not shown);
View graphically pump performance over time;
Request the current status of the pump 102 (including what insulin delivery is currently in progress, battery status, alarm conditions, insulin reservoir level, etc).

The control unit 200 is also enabled for internet connectivity, e.g. by a wireless radio connection such as Bluetooth™ or Wi-Fi between the handset and remote internet connected devices. The internet connectivity enables two-way patient support either directly or via an intermediate internet connected device such as a PC, laptop or mobile device.

Figure 3:
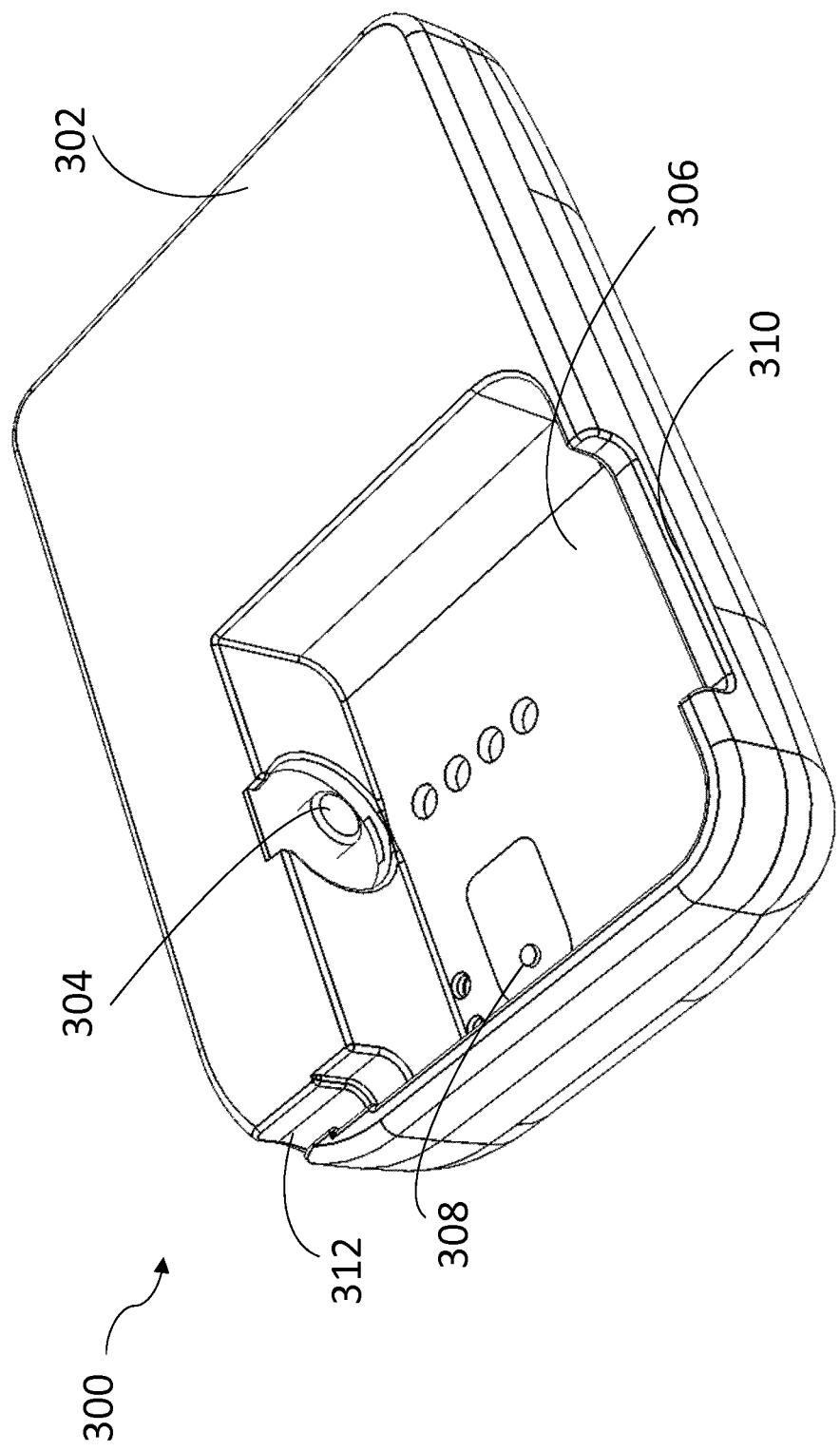
FIG. 3 shows a disposable pump part of the wearable part.
Figure 4:
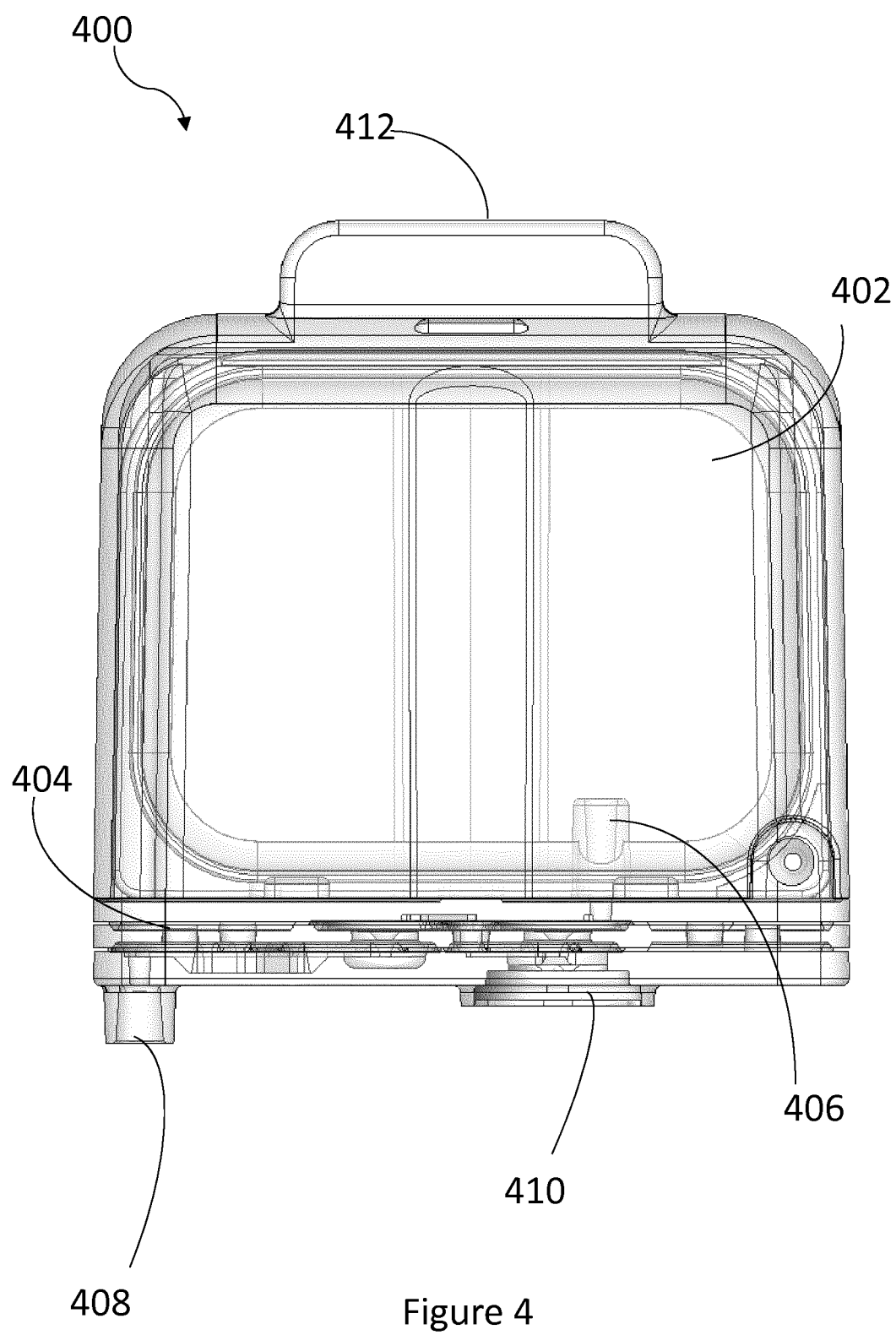
FIG. 4 shows a cartridge of the pump.
Figure 5:
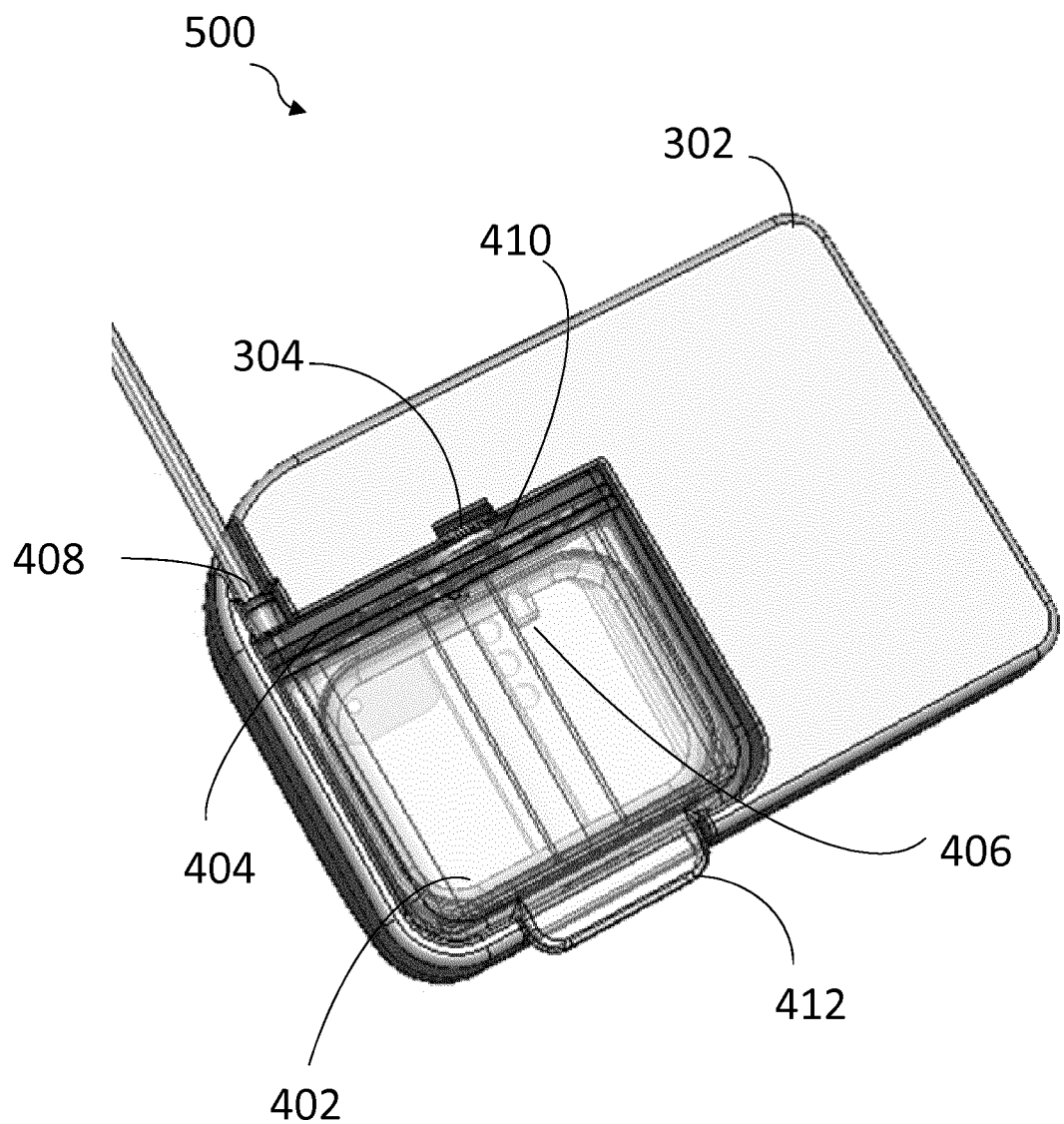
FIG. 5 shows the pump with the cartridge inserted into the disposable pump part.

Parts of the pump are shown in more detail in FIGS. 3, 4 and 5. FIG. 3 shows a durable pump part; FIG. 4 shows a cartridge containing fluid and FIG. 5 shows the durable pump part with the cartridge attached. The durable pump part is used to pump fluid from the cartridge. The skilled reader will appreciate that only the features necessary for an understanding of the invention are shown in the figures.

FIG. 3 shows a durable pump part 300. The durable pump part comprises a housing 302 with a recess 306 into which, in use, a cartridge can be inserted. The durable pump part further comprises an outlet channel 312 through which fluid is pumped, a retaining feature 310 for retaining the cartridge within the recess 306, and a switch 308 for activating the pump. The form and function of the switch 308 in particular are discussed in more detail below. The housing 302 further comprises an aperture through which a drive member 304 projects. An actuator within the housing moves the drive member 304 in reciprocating motion.

The drive member is used here to refer to any drive component that moves back and forth in linear motion and may, for example, be a piston. The piston may be a cylinder which extends through the aperture in the housing. Alternatively, the drive member may be a disc or other component driven by a rotatable cam, where the cam extends through the aperture in the housing such that the drive member remains on the side of the aperture opposite the actuator. The reciprocating drive member may be rigid, or may form part of a flexible membrane covering the aperture. The aperture is preferably sealed. The drive member may be sealed within the aperture, or alternatively the drive member may be sealed beneath a membrane covering the aperture. In this way the drive member is said to project from the aperture regardless of whether the drive member moves the sealed boundary of the housing.

FIG. 4 shows a cartridge 400. The term 'cartridge' is used here to refer to any fluid container for ready connection to and disconnection from the housing 302. The cartridge comprises a reservoir 402 for storing a fluid. The fluid may be a liquid therapeutic product, for example insulin. The cartridge further comprises a pumping chamber 404, an inlet valve 406 and an outlet valve 408. The inlet valve provides selective fluid communication between the pumping chamber and the reservoir 402. The cartridge further comprises a membrane 410, the displacement of which changes the volume of the pumping chamber.

The cartridge 400 can be removably attached to the housing 302 in FIG. 3 by inserting the cartridge 400 into the recess 306. The recess and cartridge are similarly shaped such that the cartridge fits snugly within the recess. The cartridge 400 has a retaining feature 412 corresponding to the housing retaining feature 310, and the two retaining features cooperate for the secure retention and ready removal of the cartridge 300 from the housing 402. For example, the two retaining features 310, 412 may couple together using a snap fit type connection. The skilled reader will appreciate that other methods of attachment could be used without departing from the scope of the claims appended hereto. For example the cartridge may be flush mounted to a surface of the housing, rather than being inserted into a recess.

FIG. 5 shows a pump 500, comprising the durable pump part 300 and the cartridge 400. Like parts are numbered with like numerals from the earlier figures. The cartridge 400 is attached to the housing 302 (i.e. inserted within the recess 306) such that the drive member 304 is operatively coupled to the cartridge membrane 410 for delivering a supply of fluid from the reservoir 402 to the outlet valve 408.

Fluid is pumped from the reservoir 402 to the outlet 408 as follows:

The actuator drives the drive member 304 in reciprocal motion. The drive member 304 in turn moves the pumping chamber membrane 410 to which it is coupled, which changes the volume of the pumping chamber 404. The inlet valve is opened, the outlet valve is closed, and when the drive member moves the membrane in a direction such that the volume of the pumping chamber 404 is increased, fluid is drawn in from the reservoir 402 through the inlet valve 406 and into the pumping chamber 404. The inlet valve is closed, the outlet valve is opened, and when the drive member moves the membrane in the other direction such that the volume of the pumping chamber 404 is decreased, fluid is forced out of the chamber 404 through the outlet valve 408. The outlet valve 408 may lead to an infusion set 106 as in FIG. 1, through which the fluid is infused into a patient.

The switch 308 for activating the pump will now be described in more detail. The switch is positioned on the durable pump part 300 such that attachment of the cartridge 400 to the housing 302 causes activation of the switch. In FIG. 3, the switch 308 is positioned on a surface of the housing within the recess 306. In this way, when the cartridge 400 is inserted into the recess 306, the cartridge 400 activates the switch 308 by pressing against it.

It will be appreciated that the switch can be positioned anywhere in which insertion of the cartridge will cause actuation of the switch. For example, the switch may be positioned on a side of the recess 306 such that a side of the cartridge 400 presses against the switch when the cartridge is inserted into the recess. Alternatively, the switch may be positioned on the housing retaining feature 310 such that when the cartridge 400 is attached to the housing 302 and the housing retaining feature 310 and cartridge retaining feature 412 co-operatively secure the cartridge in place, the switch is activated.

The switch 308 may be a contact switch, biased towards a raised, "off" position, so that when no pressure is applied the switch is not activated. For example, the switch may be spring-loaded. Therefore when there is no cartridge in the recess, as in FIG. 3, the switch is in the "off" position. Insertion of the cartridge into the recess, as in FIG. 5, applies pressure to the switch 308 and moves it to a depressed, "on" position, thereby activating the switch. When the cartridge 400 is removed from the housing 302, the switch returns to the "off" position.

However, the skilled person will appreciate that other types of switch may be used. For example, the switch may be a slide switch positioned on an edge of the recess 306, such that inserting the cartridge 400 into the recess 306 causes actuation of the switch. In further alternative embodiments, the switch 308 may be magnetic, reacting to a magnet suitably located in the cartridge 400 on insertion of the cartridge 400 into the recess 306. The skilled reader will appreciate that many types of switch could be used without departing from the scope of the claims.

Figure 6:
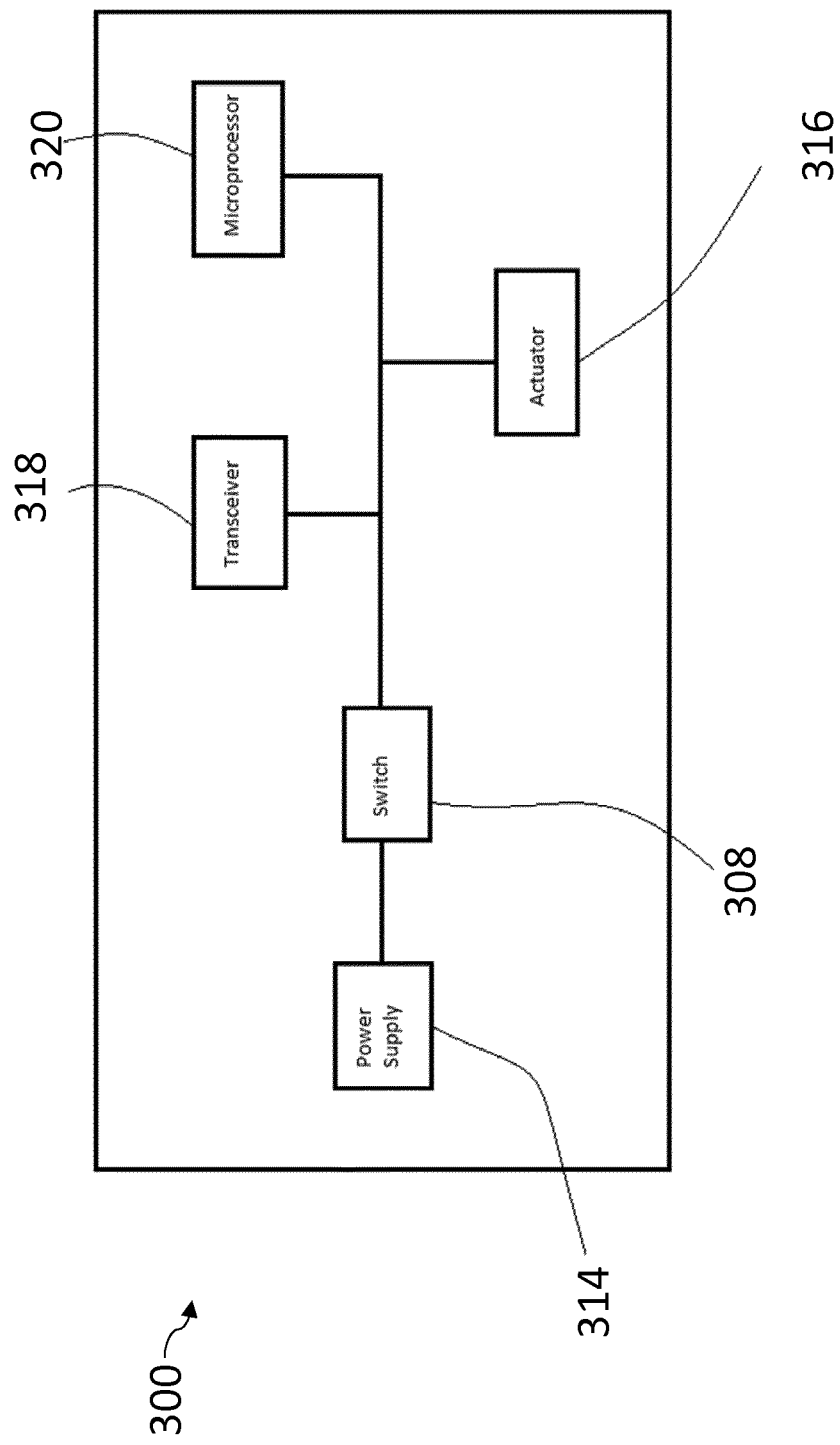
FIG. 6 shows a schematic representation of components of the pump.

FIG. 6 shows a schematic view of certain components of the durable pump part 300. The durable part 300 contains: a power supply 314, an actuator 316, a wireless transceiver 318 and a microprocessor 320.

The power supply 314 powers the pump part 300 and may be a battery, for example. In an embodiment the battery is rechargeable.

The microprocessor 320 controls the durable pump part 300, and is operatively coupled to the transceiver 318 to wirelessly transmit to and receive control signals from the control unit 200. The microprocessor 320 is further operatively coupled to the actuator 316, in order to drive the driving member in reciprocal motion as explained above, thus pumping fluid from the reservoir 402 to the outlet valve 408. The pump does not have a user interface. As explained above, operation of the pump is instead controlled wirelessly using the control unit 200. This reduces the power requirements of the durable pump part 300, and allows the power supply 314 to be recharged less frequently. Further, the absence of a user interface allows the wearable parts of the system to be more compact, so they can be worn discreetly.

In the illustrated embodiment, the power supply 314 is operatively coupled to the other components in the durable pump part 300 via the switch 308. Thus activation of the switch 308 connects the power supply 314 to the microprocessor 320, the transceiver 318 and the actuator 316. The microprocessor 320 can then control the transceiver 318 and the actuator 316 as necessary. For example, the microprocessor 320 may control the transceiver 316 such that the durable pump part 300 is made available for pairing over a BlueTooth™ communications protocol. Deactivation of the switch 308 in this embodiment decouples those components from the power supply 314 and immediately deactivates them.

Alternatively, the switch 308 may not physically couple and decouple the power supply 314 from other components of the durable pump part 300. In these alternative embodiments, activation and deactivation of the switch 308 may cause control signals to be sent to one or more of the components to activate them. For example, when the switch is activated, an activation control signal may be sent to the microprocessor 320, which can then control the transceiver 318 and actuator 316 as necessary. For example, on receiving this control signal the microprocessor 320 may activate the transceiver 318 to make the durable pump part 300 available for pairing over a BlueTooth™ communications protocol. The microprocessor 320 may control the actuator 316 to begin pumping fluid from the cartridge 400.

Deactivation of the switch 308 in these embodiments may cause further control signals to be sent to the components to deactivate them. For example, a deactivation signal may be sent to the microprocessor 320 which then deactivates the other components as necessary. The microprocessor 320 may control the actuator 316 to be immediately deactivated, such that the actuator does not attempt to pump fluid in the absence of a cartridge. In further embodiments, the deactivation signal may cause the microprocessor 320 to deactivate the transceiver 318 only once a current or planned wireless signal has been transmitted or received.

According to one embodiment, the pump is operated as follows:

A cartridge 400 is inserted into the recess 306 when the user starts using the pump. Insertion of the cartridge 400 activates the switch 308 (e.g. moves it to an "on" position), which activates the pump.

During operation the microprocessor 320 may control the actuator 316 based on information received over the wireless connection from the control unit 200, or from information stored in a memory (not illustrated). When activated, the pump is made available for pairing via Bluetooth™. The control unit 200 actively searches for a pump to pair with and, once the durable pump part 300 becomes available for pairing, the control unit 200 forms a wireless connection with the durable pump part 300. The transceiver 318 of the pump sends information to, and receives information from, the control unit 200 over this wireless connection. For example, the transceiver 316 may transmit information relating to the operational status of the durable pump part 300, the quantity of fluid which has been pumped, etc.

The actuator pumps fluid from the reservoir to the outlet 104 in FIG. 1, which then flows into the infusion system 106, and is infused into a patient.

For example, the rate of flow of fluid to the patient can be controlled by a user at the control unit 200 using the tactile user interface 204. This information can be transmitted wirelessly to the transceiver 606 in the pump. The information is processed by the microprocessor which controls movement of the actuator accordingly.

Information recording the movement of the actuator can be processed by the microprocessor and transmitted over the wireless network via the transceiver 606 from the pump to the control unit 200. The information is received by the control unit 200 and displayed to the user on the user interface 202.

When the user wants to stop using the pump, for example when the infusion is complete or when all of the fluid from the cartridge has been used, the user can detach the cartridge from the housing by removing it from the recess. This will move the cartridge away from the switch 308, deactivating it as described above. The durable pump part 300 is then deactivated as explained above.

In an alternative embodiment, the removal of the cartridge may not cause the switch to deactivate. In this case the pump may stay on after the removal of the cartridge.

There is provided a fluid delivery system, comprising a pump for pumping fluid from a cartridge to an outlet. The pump comprises a housing, a cartridge which can be removably attached to the housing, and a switch for activating the pump. The switch is arranged such that attaching the cartridge to the housing activates the switch to automatically activate the pump. In this way, power can be conserved in the pump by ensuring that it is only activated when there is a supply of fluid to be pumped (i.e. from the cartridge).

Although the invention has been described above with reference to one or more embodiments, it will be appreciated that various changes or modifications may be made without departing from the scope of the invention as defined in the appended claims.

The invention claimed is:

1. A fluid delivery system, comprising:
   a pump comprising:
      a housing;
      a cartridge for storing fluid, the cartridge removably attachable to the housing;
      a switch for activating the pump, wherein the switch is arranged such that attaching the cartridge to the housing activates the switch to automatically activate the pump; and
      a transceiver for wirelessly connecting to a control unit, wherein the pump is wirelessly connectable to the control unit for controlling the pump;
   wherein the automatic activation of the pump comprises activation of the transceiver that makes the pump available for pairing with the control unit over a Bluetooth™ or other radio frequency near field communications protocol.

2. The fluid delivery system according to claim 1, where the switch is a contact switch positioned on the housing such that attaching the cartridge to the housing causes actuation of the switch.

3. The fluid delivery system according to claim 2, wherein the switch is resiliently biased towards an off position.

4. The fluid delivery system according to claim 3, wherein the switch is spring-loaded.

5. The fluid delivery system according to claim 1, wherein the switch is positioned on a surface of the pump against which the cartridge attaches.

6. The fluid delivery system according to claim 1, wherein the housing comprises a recess into which the cartridge can be inserted.

7. The fluid delivery system according to claim 1, wherein detaching the cartridge from the housing automatically causes the pump to be deactivated.

8. The fluid delivery system according to claim 1, wherein the pump does not comprise a user interface.

9. The fluid delivery system according to claim 1, wherein the pump further comprises a microprocessor and activation of the pump comprises activation of the microprocessor.

10. The fluid delivery system according to claim 1, wherein the pump further comprises an actuator and activation of the pump comprises activation of the actuator.

11. The fluid delivery system according to claim 10 wherein:
   the actuator comprises a drive member; and
   the switch is arranged such that attaching the cartridge to the housing such that the drive member is operatively coupled to the cartridge causes the switch to be activated.

12. The fluid delivery system according to claim 1, further comprising the control unit for controlling the pump.

13. The fluid delivery system according to claim 1, wherein the fluid delivery system is an infusion system for delivering fluid to a patient.

\* \* \* \* \*